United States Patent
Russ

(10) Patent No.: US 10,813,830 B2
(45) Date of Patent: Oct. 27, 2020

(54) SEXUAL AID AND PROTECTIVE DEVICE

(71) Applicant: Steven T. Russ, Garden Valley, ID (US)

(72) Inventor: Steven T. Russ, Garden Valley, ID (US)

( * ) Notice: Subject to any disclaimer, the term of this patent is extended or adjusted under 35 U.S.C. 154(b) by 0 days.

(21) Appl. No.: 16/370,335

(22) Filed: Mar. 29, 2019

(65) Prior Publication Data

US 2019/0298603 A1    Oct. 3, 2019

Related U.S. Application Data

(60) Provisional application No. 62/650,843, filed on Mar. 30, 2018.

(51) Int. Cl.
*A61H 19/00* (2006.01)
*A61F 5/41* (2006.01)

(52) U.S. Cl.
CPC ............. *A61H 19/50* (2013.01); *A61H 19/34* (2013.01); *A61F 2005/411* (2013.01)

(58) Field of Classification Search
CPC ........ A61H 19/34; A61H 19/32; A61H 19/50; A61H 2201/165; A61H 19/40; A61H 19/00; A61F 5/41; A61F 6/04; A61F 2005/411; A61F 2005/414
See application file for complete search history.

(56) References Cited

U.S. PATENT DOCUMENTS

2009/0069629 A1\* 3/2009 Uson Calvo ........... A61H 19/34
                                                                600/38
2016/0271007 A1    9/2016 Kolkind

FOREIGN PATENT DOCUMENTS

GB            2549690 A     1/2017

\* cited by examiner

*Primary Examiner* — Christine H Matthews
(74) *Attorney, Agent, or Firm* — Shaver & Swanson, LLP; Scott D. Swanson

(57) ABSTRACT

A sexual aid and protective device for use in sexual intercourse that is positioned on a wearer's pelvic area, superior to the wearer's genital area, specifically covering the pubic bone. The device comprises a base, which further comprises a ring that is configured to encircle the wearer's penis or phallic device, with a tab that attaches to the ring for easy removal and additional stimulation of the wearer's partner, and a raised area, generally an ellipsoidal shape, that protects the wearer while simultaneously providing stimulation to the wearer's partner.

13 Claims, 3 Drawing Sheets

SEXUAL AID AND PROTECTIVE DEVICE

PRIORITY/CROSS-REFERENCE TO RELATED APPLICATIONS

This application claims the benefit of U.S. Provisional Application No. 62/650,843, filed Mar. 30, 2018, the disclosure of which is incorporated by reference.

TECHNICAL FIELD

The disclosure generally relates to the field of sexual aids. Particular embodiments relate to protective devices for use during sexual intercourse.

BACKGROUND OF THE INVENTION

Humans have sexual intercourse in a variety of positions. One such position is when the woman is in an active position, such that the woman is on top of her partner. In slang terminology this position is called the 'woman on top' or 'cowgirl' position. The inventor has discovered that while in this position, if the woman is aggressive during intercourse, the male's pubic bone and covering tissue can be injured, such as bruised, by the woman's movements in stimulating her genital area on her partner's pubic bone. Accordingly, what is needed is a protective device to protect the wearer's pubic bone while enhancing the stimulation of the woman, who is on top.

SUMMARY

The purpose of the summary is to enable the public, and especially the scientists, engineers, and practitioners in the art, who are not familiar with patent or legal terms or phraseology, to determine quickly from a cursory inspection, the nature and essence of the technical disclosure of the application. The summary is neither intended to define the inventive concept(s) of the application, which is measured by the claims, nor is it intended to be limiting as to the scope of the inventive concept(s) in any way.

What has been invented is a sexual aid and protective device to be worn during sexual intercourse that is positionable on the wearer's pelvic area, specifically protecting the wearer's pubic bone and covering tissue. The device includes a base, generally ellipsoidal or rectangular in shape. The base has a ring that defines an opening. In a preferred embodiment, the ring defines a round or generally elliptical opening, configured for insertion of a male penis or other phallic object, such as a dildo. For example, the dildo of a strap-on-dildo apparatus (a dildo utilized in a harness worn by the user) can be placed through the opening. The ring is generally located proximate to an end of the apparatus. The ring is made of a material that is sufficiently flexible to be stretched to facilitate a dildo or penis having a larger circumference than that of the ring.

In a preferred embodiment, the sexual aid and protection device includes a tab attached proximate to the ring. The tab provides additional stimulation for the perineum of the partner of the wearer, and also acts as a grip for the wearer to grab hold of and remove the ring from the penis or other phallic object.

The device has a raised area that is made of an elastic material. The raised area is configured generally in the shape and dimensions of the average female's pubic region. The raised area provides an additional stimulation area for the partner of a wearer of the device in the same region as the pubis but without focusing on replacing the male penis or an imitator thereof. The device provides a secondary pleasure area for a sexual partner of the wearer without removing the ability of the dildo or penis to contact the vagina. The raised area can include a ribbed, knobbed, or otherwise textured or contoured area to enhance stimulation of a wearer's female partner. The raised area extends from an area near to the ring toward the second end of the base. The raised area generally has sloping transitions from the base to an apex of the raised area. The raised area is preferably concave to create a cavity to provide a suction effect when in use. This suction effect, in combination with the ellipsoidal shape of the raised area, allows the device to remain in position without the need for a harness, belt, band, strap, or other restraining feature. In a preferred embodiment, the base extends beyond the raised area to provide a flange around the raised area. The flange provides stability and further friction between the base and the wearer's pelvic area. In an alternative embodiment, the raised area extents to the edge of the base.

In use the wearer positions the wearer's penis, or other phallic object, through the ring of the device. The device is worn such that the second end of the device extends toward the wearer's upper torso, thus providing protection to the wearer's pubic bone and covering tissue. The raised area corresponds to a woman's clitoris and the labia minora, above the opening of the urethra and superior to the vagina, when a woman is engaged in an active sexual position facing her partner. The tab is preferably located below the ring in the area corresponding to the woman's perineum. In this manner a wearer's penis, or other phallic device, protruding through the opening will be positioned for insertion into the vagina, with the raised area aligned with the woman's clitoris and the labia minora and the tab positioned on the perineum. The wearer may then remove the device by grabbing the tab and removing the ring from the penis or phallic object.

Other features and advantages of the presently disclosed and claimed inventive concept(s) will become readily apparent. To those skilled in this art, the following details describe preferred embodiments of the inventive concept(s), simply by way of illustration of the best mode contemplated by carrying out the inventive concept(s). As will be realized, the inventive concept(s) is(are) capable of modification in various obvious respects all without departing from the inventive concept(s). Accordingly, the drawings and description of the preferred embodiments are to be regarded as illustrative in nature, and not as restrictive in nature.

DETAILED DESCRIPTION

Figure 1:
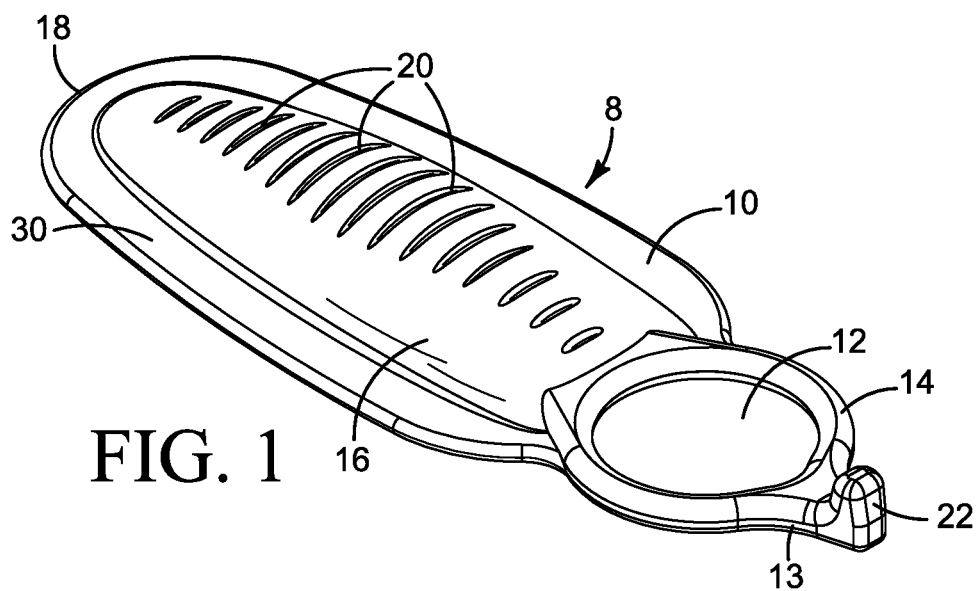
FIG. 1 is an isometric view of the top of an embodiment of the sexual aid and protective device.
Figure 2:
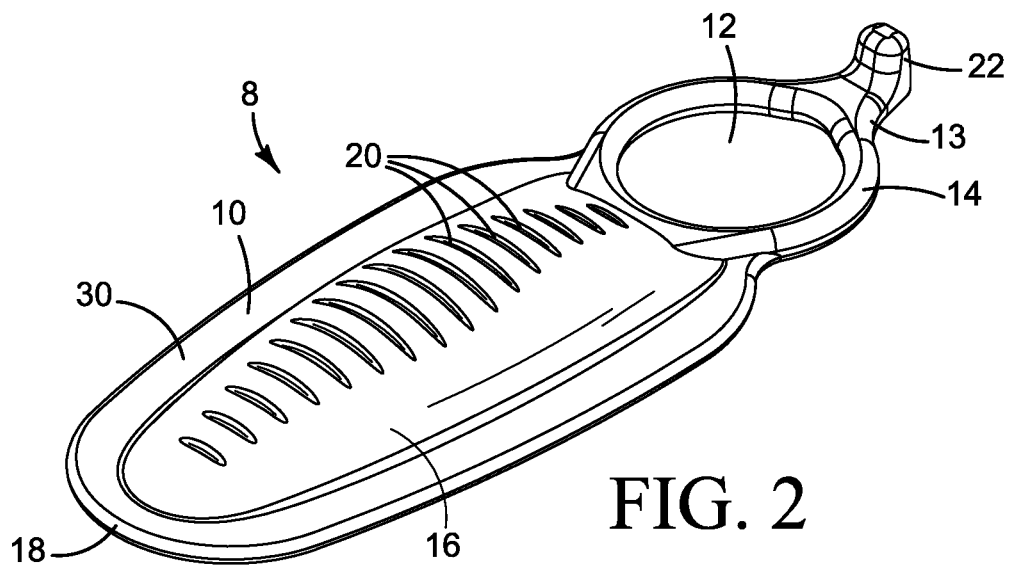
FIG. 2 is another isometric view of the top of an embodiment of the sexual aid and protective device.

While the presently disclosed inventive concept(s) is(are) susceptible to various modifications and alternative constructions, certain illustrated embodiments thereof have been shown in the drawings and will be described below in detail. It should be understood, however, that there is no intention to limit the inventive concept(s) to the specific form disclosed, but, on the contrary, the presently disclosed and claimed inventive concept(s) is(are) to cover all modifications, alternative constructions, and equivalents falling within the spirit and scope of the inventive concept(s), as defined herein.

In the following description, and in the figures, like elements are identified with like reference numerals. The use of "e.g.," "etc," and "or" indicates non-exclusive alternatives without limitation, unless otherwise noted. The use of "including" means "including, but not limited to," unless otherwise noted.

FIGS. 1 through 12 illustrate a preferred embodiment of the sexual aid and protective device 8. In the illustrated preferred embodiment, the device includes a base 10. The base 10 generally has an elliptical shape. However, a rectangular shape or any other shape can be used that comports with the inventive concepts disclosed herein. The base 10 has a ring 14 defining an opening 12 near the first end 13 of the base. An average width of the opening 12 is about 1⅜ inches. The ring can be constructed using materials of various elasticizes to accommodate the wearer's different penis or phallic dimensions. The ring 14 around the opening 12 is configured to be placed around the penis or phallic device of the wearer, and is generally constructed of an elastic material to allow for a comfortable attachment to the wearer. This elastic material also allows the ring 14 to stretch to accommodate larger items inserted into the opening 12, specifically to accommodate penises or phallic devices with a larger circumference.

The base includes a raised area 16 that generally extends from the ring 14 to the opposing (second) end 18 of the base 10. A base flange 30 extends outward from the raised area as to provide further stability and/or friction contact area on the wearer.

In a preferred embodiment, the base 10 is of a length so as when the ring 14 is placed on a male's penis or other phallic type projection, the raised area 16 is positioned over the wearer's pubic bone and pelvic area. The raised area 16 is configured so as to correspond to the general shape and length of the female genitalia. The raised area 16 is preferably constructed of an elastic material that can be compressed and regain its shape after the compression force is removed, such as silicone, latex, rubber, plastic, or rubbers and plastics containing phthalates. This raised area 16 provides padding and protection for the wearer of the device and provides compression and enhanced stimulation to the wearer's partner.

In a preferred embodiment, a tab 22 is attached to the first end 13 of the sexual aid and protective device 8, proximate to the ring 14. The tab 22 acts as a handle for the wearer to grab to remove the ring 14 from the wearer's penis or phallic device. The tab 22 also acts as a perineum tickler for the wearer's partner. The tab can be in a variety of shapes and/or sizes.

In a preferred embodiment, the raised area includes a plurality of ribbed projections 20. In alternate embodiments, the raised area 16 can include surface texture to provide further friction between the raised area 16 of the device and the genitals of the wearer's partner, including, but not limited to, being textured. In alternate embodiments, the device can include a vibrating mechanism for providing vibrations to the device.

Figure 4:
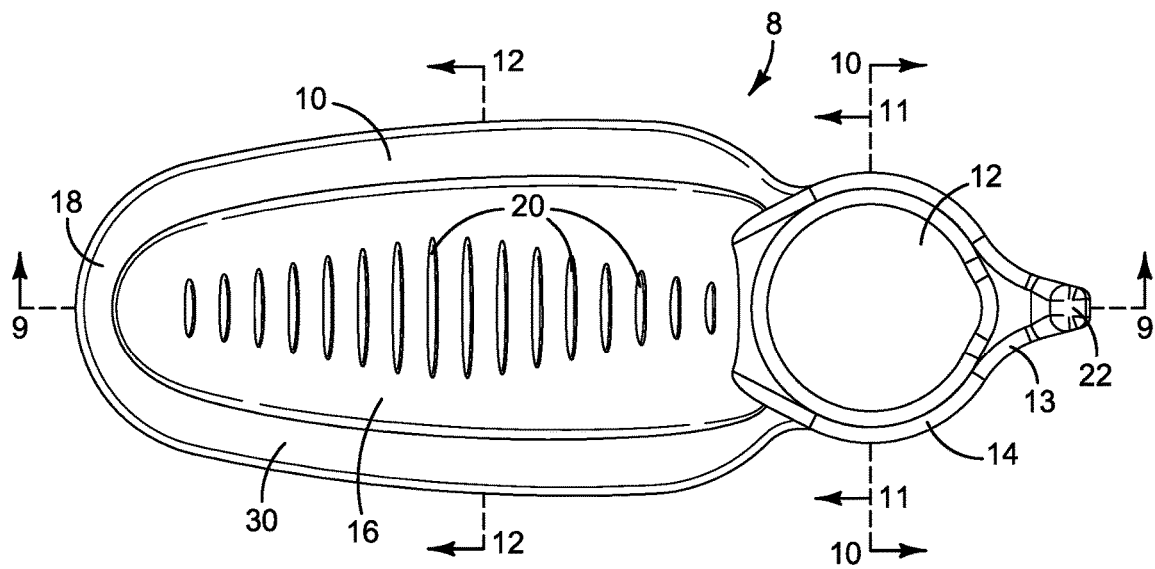
FIG. 4 is a top view of an embodiment of the sexual aid and protective device.

FIG. 4 is a top view of a preferred embodiment of the sexual aid and protective device 8. The depicted plurality of ribbed projections 20 are preferably different lengths, decreasing in length the farther the plurality of ribbed projections 20 are from the center of the raised area 16.

Figure 3:
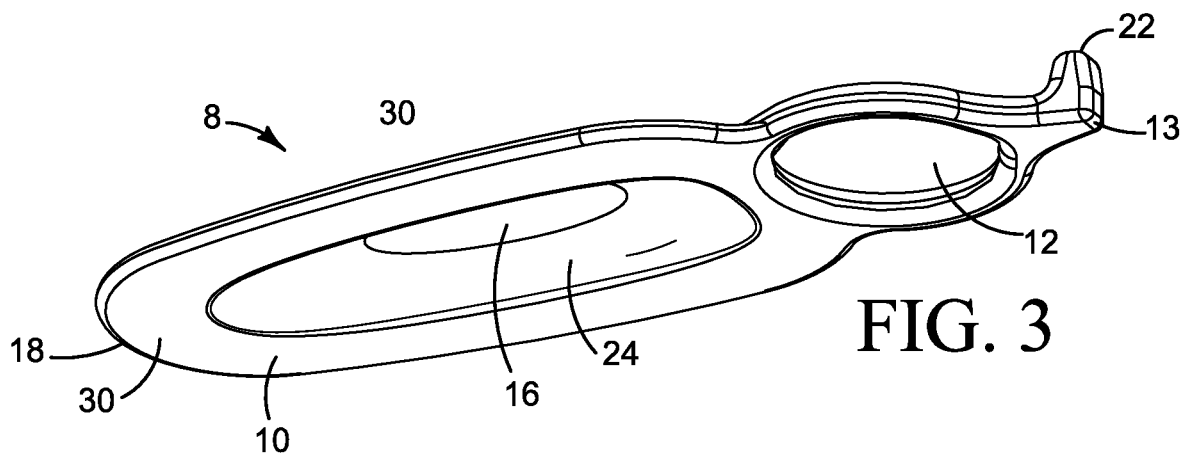
FIG. 3 is a bottom perspective view of the bottom of an embodiment of the sexual aid and protective device.

FIG. 3 illustrates the bottom of the sexual aid and protective device 8. In a preferred embodiment, the bottom side of the raised area 16 is concave to create a cavity 24 from the base 10 to provide a suction effect when in use. The base flange 30 encircles the cavity 24 to provide structural support. In alternate embodiments, the raised area 16 can be solid and the base 10 can span the entirety of the bottom of the sexual aid and protective device 8.

Figure 5:
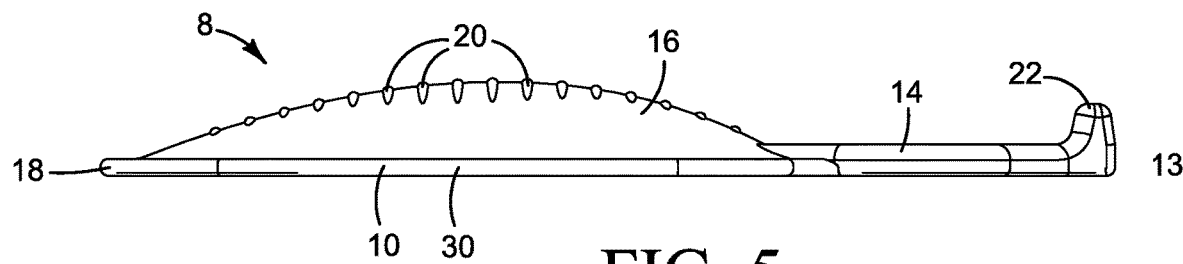
FIG. 5 is a side view of an embodiment of the sexual aid and protective device.

FIG. 5 is a side view of a preferred embodiment of the sexual aid and protective device 8. In a preferred embodiment, the base 10 is generally planar and preferably has a hollow cavity as shown in FIG. 6.

Figure 6:
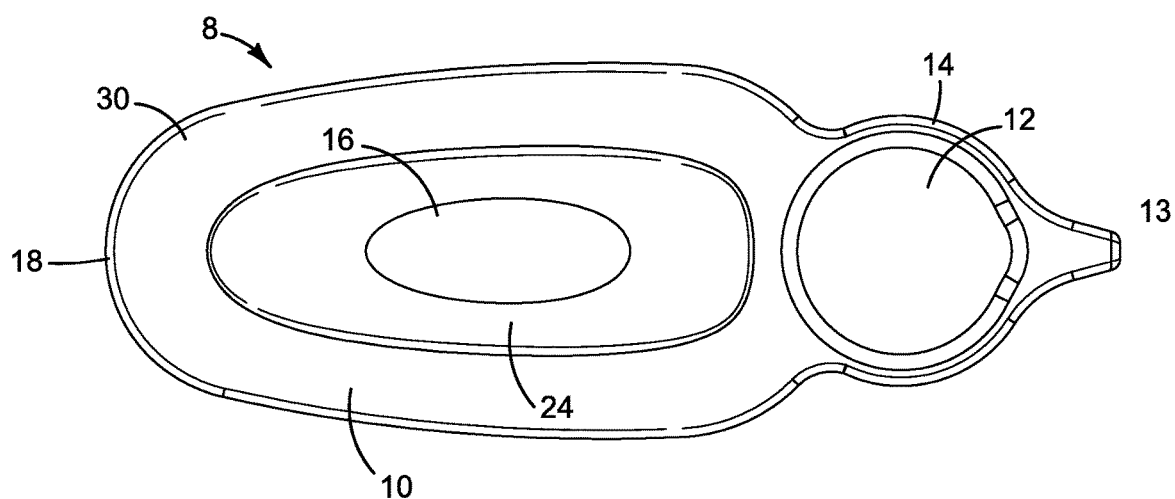
FIG. 6 is a bottom view of an embodiment of the sexual aid and protective device.

FIG. 6 is a bottom view of a preferred embodiment of the sexual aid and protective device 8. FIG. 6 depicts the hollow cavity 24 that extends through the base 10 and extends into the raised area 16.

Figure 7:
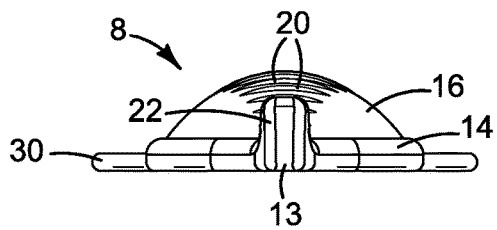
FIG. 7 is an end view of an embodiment of the sexual aid and protective device.

FIG. 7 is one end view of a preferred embodiment of the sexual aid and protective device 8. FIG. 7 illustrates the height of the various sections of the device.

Figure 8:
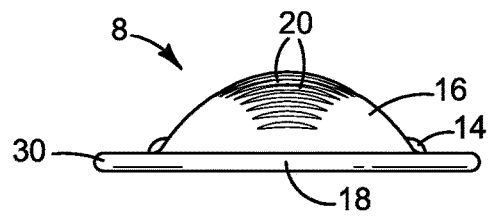
FIG. 8 is another end view of an embodiment of the sexual aid and protective device.

FIG. 8 is another end view of a preferred embodiment of the sexual aid and protective device 8. FIG. 8 illustrates the height of the various sections of the device.

Figure 9:
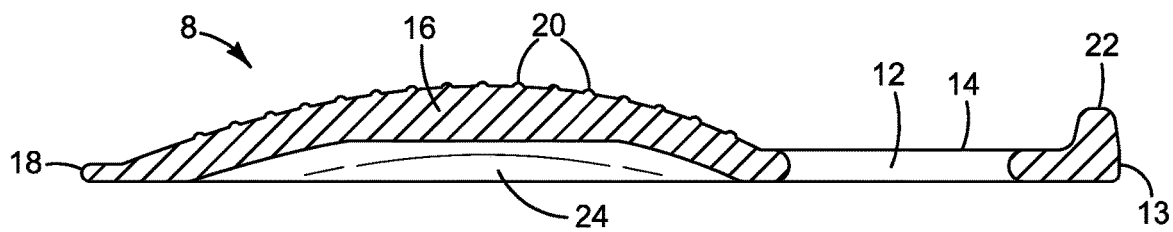
FIG. 9 is a cross section view along line 9 depicted in FIG. 4 of an embodiment of the sexual aid and protective device illustrating a midline cross section of the length of the sexual aid and protective device.

FIG. 9 is a side view of a longitudinal cross section along line 9 depicted in FIG. 4 of a preferred embodiment of the sexual aid and protective device 8. The longitudinal cross section is through the base 10, the raised area 16, the ring 14, and the tab 22.

Figure 10:
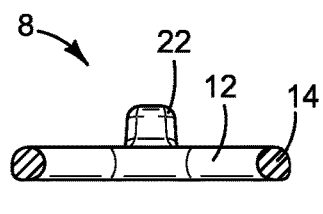
FIG. 10 is a cross section view along line 10 depicted in FIG. 4 of an embodiment of the sexual aid and protective device illustrating a midline cross section of the width of the ring viewed toward the tab.

FIG. 10 is an end view of the ring 14 cross section along line 10 depicted in FIG. 4 of a preferred embodiment of the sexual aid and protective device 8.

Figure 11:
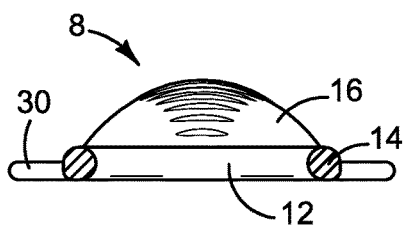
FIG. 11 is a cross section view along line 11 depicted in FIG. 4 of an embodiment of the sexual aid and protective device illustrating a midline cross section of the width of the ring viewed toward the raised area.

FIG. 11 is an end view of the ring 14 cross section along line 11 depicted in FIG. 4 of a preferred embodiment of the sexual aid and protective device 8.

Figure 12:
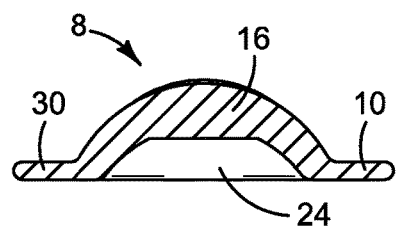
FIG. 12 is a cross section view along line 12 depicted in FIG. 4 of the sexual aid and protective device illustrating a midline cross section of the width of the raised area.

FIG. 12 is an end view along line 12 cross section depicted in FIG. 4 of the raised area 16 in a preferred embodiment of the sexual aid and protective device 8.

The device can be made utilizing a variety of techniques including, 3D printing, injection molding, silicone molding, or any other known or future technology.

While certain exemplary embodiments are shown in the Figures and described in this disclosure, it is to be distinctly understood that the presently disclosed inventive concept(s) is(are) not limited thereto, but may be variously embodied to practice within the scope of this disclosure. From the foregoing description, it will be apparent that various changes may be made without departing from the spirit and scope of the disclosure as defined herein.

The invention claimed is:

1. A sexual aid and protective device comprising:
a base, said base defining a width and a length, said base comprising a first end and a second end, said base comprising a top side and a bottom side;
wherein said base comprises a ring in said base proximate to said first end of said base wherein said ring defines an opening comprising a circumference, wherein said ring is configured to encircle a penis or phallic device of a wearer, wherein said ring comprises an elastic material capable of stretching to expand the circumference of said ring;
wherein said top side comprises a raised area, wherein said raised area extends from proximate to said ring toward said second end of said base, wherein said raised area comprises a sloping transition from said base to a ridge of said raised area, wherein said raised area comprises an elastic material;
wherein said bottom side of said base is generally flat so as to be configured to be positioned on the wearer's pubic region when the wearer's penis or phallic device is positioned through said ring;
wherein said second end of said base extends toward the waist line of the wearer such that said base at least partially covers the pubic region of the wearer when the wearer's penis or phallic device is positioned through said ring and said base is positioned on the wearer's pubic region.

2. The sexual aid and protective device of claim 1, wherein said opening comprises a general shape and size to fit an average penis.

3. The sexual aid and protective device of claim 1, wherein said elastic material comprises a material having a Shore A value between 15 and 50.

4. The sexual aid and protective device of claim 1, wherein said base comprises a stability flange around said raised area.

5. The sexual aid and protective device of claim 1, wherein said raised area comprises a vibrating mechanism.

6. The sexual aid and protective device of claim 1, wherein said raised area comprises a plurality of ribbings extending across a surface of said raised area.

7. The sexual aid and protective device of claim 1, wherein said first end of said base comprises a tab extending generally perpendicular from said base.

8. The sexual aid and protective device of claim 7, wherein said tab is configured for grasping by a user.

9. A sexual aid and protective device comprising:
a base, said base defining a width and a length, said base comprising a first end and a second end, said base comprising a top side and a bottom side;
wherein said base comprises a ring in said base proximate to said first end of said base, wherein said ring defines an opening comprising a circumference, wherein said opening comprises a general shape and size to fit an average penis, wherein said ring is configured to encircle the penis or phallic device of a wearer, wherein said ring comprises an elastic material capable of stretching to expand the circumference of said ring;
a tab, wherein said tab is attached to said first end and extends from the circumference of said ring, wherein said tab is configured for grasping by a wearer to remove said ring and wherein said tab is configured to stimulate a partner of the wearer;
wherein said top side comprises a raised area, wherein said raised area extends from proximate to said ring toward said second end of said base, wherein said raised area comprises a sloping transition from said base to a ridge of said raised area, wherein said raised area comprises an elastic material;
wherein said bottom side of said base is generally flat so as to be configured to be positioned on the wearer's pubic region when the wearer's penis or phallic device is positioned through said ring;
wherein said second end of said base extends toward the waist line of the wearer such that said base at least partially covers the pubic region of the wearer when the wearer's penis or phallic device is positioned through said ring and said base is positioned on the wearer's pubic region.

10. The sexual aid and protective device of claim 9, wherein said base comprises a vibrating mechanism.

11. The sexual aid and protective device of claim 9, wherein said raised area is concave.

12. The sexual aid and protective device of claim 9, wherein said elastic material comprises a material having a Shore A value between 15 and 50.

13. The sexual aid and protective device of claim 9, wherein said raised area comprises a plurality of ribbings extending across a surface of said raised area.

* * * * *